(12) United States Patent
Hauck

(10) Patent No.: US 9,532,881 B2
(45) Date of Patent: Jan. 3, 2017

(54) MEMORY MATERIAL IMPLANT SYSTEM AND METHODS OF USE

(71) Applicant: Brian Albert Hauck, Windsor, CA (US)

(72) Inventor: Brian Albert Hauck, Windsor, CA (US)

(*) Notice: Subject to any disclaimer, the term of this patent is extended or adjusted under 35 U.S.C. 154(b) by 231 days.

(21) Appl. No.: 14/071,493

(22) Filed: Nov. 4, 2013

(65) Prior Publication Data

US 2014/0067073 A1    Mar. 6, 2014

Related U.S. Application Data

(63) Continuation-in-part of application No. 13/964,039, filed on Aug. 10, 2013, now abandoned.

(60) Provisional application No. 61/725,030, filed on Nov. 12, 2012, provisional application No. 61/837,703, (Continued)

(51) Int. Cl.
| | |
|---|---|
| *A61B 17/88* | (2006.01) |
| *A61F 2/44* | (2006.01) |
| *A61B 17/72* | (2006.01) |
| *A61F 2/46* | (2006.01) |
| *A61F 2/28* | (2006.01) |
| *A61F 2/30* | (2006.01) |

(52) U.S. Cl.
CPC ......... *A61F 2/4455* (2013.01); *A61B 17/7266* (2013.01); *A61B 17/8825* (2013.01); *A61F 2/4465* (2013.01); *A61F 2/4611* (2013.01); *A61F 2002/2817* (2013.01); *A61F 2002/2835* (2013.01); *A61F 2002/302* (2013.01); *A61F 2002/3055* (2013.01); *A61F 2002/30092* (2013.01); *A61F 2002/30116* (2013.01); *A61F 2002/30235* (2013.01); *A61F 2002/30462* (2013.01); *A61F 2002/30545* (2013.01); *A61F 2002/30555* (2013.01); *A61F 2002/30576* (2013.01); *A61F 2002/30578* (2013.01); *A61F 2002/30583* (2013.01); *A61F 2002/30588* (2013.01); *A61F 2002/30841* (2013.01); *A61F 2002/30845* (2013.01); *A61F 2002/30848* (2013.01); *A61F 2310/00023* (2013.01); *A61F 2310/00796* (2013.01)

(58) Field of Classification Search
CPC .. A61B 17/72; A61B 17/7208; A61B 17/7216
USPC ............................. 606/62–64, 279, 300, 331
See application file for complete search history.

(56) References Cited

U.S. PATENT DOCUMENTS

| | | |
|---|---|---|
| 5,716,416 A | 2/1998 | Lin |
| 5,919,235 A | 7/1999 | Husson et al. |
| 5,986,169 A | 11/1999 | Gjunter |
| (Continued) | | |

*Primary Examiner* — Ellen C Hammond
*Assistant Examiner* — Christina Negrellirodrigue

(57) ABSTRACT

Apparatus and method used to reduce the movement between vertebrae or fractured bones. The implantable device can be deformed from its shape-set configuration for ease of deployment and return to a pre-set shape upon completion of deployment. The apparatus can serve to stabilize fractured bones or as a distraction device and support structure between vertebrae. Device may be made of a material with shape memory and superelastic properties which facilitate the method of implantation. The pre-set shape of the device may include dimensions/geometries which are similar to the natural curvature of the human spine or bone without the use of hinging or connection between multiple pieces. Once deployed, the device can serve to constrain the flow of bone growth material between the inside and outside of the device.

19 Claims, 13 Drawing Sheets

Related U.S. Application Data filed on Jun. 21, 2013, provisional application No. 61/682,282, filed on Aug. 12, 2012.

(56) References Cited

U.S. PATENT DOCUMENTS

| | | | |
|---|---|---|---|
| 6,127,597 A | 10/2000 | Beyar et al. | |
| 7,604,870 B2 | 10/2009 | Chernyshov et al. | |
| 7,666,227 B2 | 2/2010 | Schaller | |
| 7,695,471 B2 | 4/2010 | Cheung et al. | |
| 7,938,860 B2 | 5/2011 | Trieu | |
| 8,162,942 B2* | 4/2012 | Coati | A61B 17/7266 606/63 |
| 8,206,423 B2 | 6/2012 | Siegal | |
| 8,328,812 B2 | 12/2012 | Siegal et al. | |
| 8,366,773 B2 | 2/2013 | Schaller et al. | |
| 8,470,043 B2 | 6/2013 | Schaller et al. | |
| 8,518,117 B2 | 8/2013 | Sack et al. | |
| 8,556,978 B2 | 10/2013 | Schaller | |
| 8,579,983 B2 | 11/2013 | Garner et al. | |
| 8,591,583 B2 | 11/2013 | Schaller et al. | |
| 2002/0109986 A1* | 8/2002 | Siegel | F21L 4/06 362/202 |
| 2003/0055505 A1 | 3/2003 | Sicotte et al. | |
| 2004/0230309 A1 | 11/2004 | DiMauro et al. | |
| 2005/0187555 A1* | 8/2005 | Biedermann | A61B 17/68 606/62 |
| 2006/0264950 A1* | 11/2006 | Nelson | A61B 17/7208 606/916 |
| 2008/0009944 A1 | 1/2008 | McGuckin, Jr. | |
| 2008/0221687 A1 | 9/2008 | Viker | |
| 2008/0269745 A1* | 10/2008 | Justin | A61B 17/7044 606/62 |
| 2009/0177207 A1 | 7/2009 | Schaller | |
| 2010/0114107 A1 | 5/2010 | Trieu | |
| 2010/0241120 A1* | 9/2010 | Bledsoe | A61B 17/7208 606/62 |
| 2011/0213463 A1 | 9/2011 | Kuslich | |
| 2011/0230967 A1 | 9/2011 | O'Halloran et al. | |
| 2011/0245924 A1 | 10/2011 | Kuslich | |
| 2011/0307064 A1 | 12/2011 | Schaller | |
| 2012/0029643 A1 | 2/2012 | Robinson | |
| 2012/0123554 A1 | 5/2012 | Fonte | |
| 2012/0330314 A1 | 12/2012 | Schaller et al. | |
| 2013/0131810 A1 | 5/2013 | Schaller et al. | |
| 2013/0190880 A1 | 7/2013 | Schaller | |
| 2013/0226187 A1 | 8/2013 | Schaller et al. | |
| 2013/0282062 A1 | 10/2013 | McGrath et al. | |
| 2014/0025171 A1 | 1/2014 | Schaller | |

* cited by examiner

2500

ACCESS TO THE MEDULLARY CANAL IS OBTAINED VIA A BONEY PROTRUSION

2510

A GUIDE WIRE IS INSERTED INTO THE ACCESS SITE AND TRAVERSED ACROSS THE FRACTURE SITE

2520

THE MEDULLARY CANAL MAY BE REAMED TO ENSURE THE IMPLANT CAN FIT WITHIN THE CANAL

2530

THE IMPLANT SYSTEM IS INSERTED INTO THE MEDULLARY CANAL AND OFF-LOADED FROM THE MANDREL

2540

THE GUIDE WIRE IS REMOVED AND TRANSVERSE BONE SCREWS MAY BE INSTALLED TO PROVIDE FRACTURE FIXATION

2550

THE ACCESS SITE IS CLOSED AND IF DEEMED NECESSARY A CAST OR OTHER STABILIZING DEVICE MAY BE USED DURING THE HEALING PROCESS

FIG. 25

MEMORY MATERIAL IMPLANT SYSTEM AND METHODS OF USE

CROSS-REFERENCE TO RELATED APPLICATIONS

This is a Continuation-In-Part of U.S. patent application Ser. No. 13/964,039 filed Aug. 10, 2013, which claims the benefit of priority to U.S. Provisional Patent Application 61/682,282 filed Aug. 12, 2012, and priority benefit is claimed for all common subject matter thereof. The benefit of priority is further claimed, for all common subject matter, to U.S. Provisional Patent Application 61/837,703 filed Jun. 21, 2013. The benefit of priority is further claimed, for all common subject matter, to U.S. Provisional Patent Application 61/725,030 filed Nov. 12, 2012. Each of which are incorporated herein by reference in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

FIELD OF THE INVENTION

The application relates to orthopedics and more particularly to bone fixation and spinal fusion devices and methods of implanting them.

BACKGROUND OF THE INVENTION

Fractured bones are among the most common orthopedic problem; about 6.8 million come to medical attention each year in the United States. Degenerative disc disease resulting in spine fusions has increased significantly and now represents approximately ½ million surgeries annually. The implantation of internal fixation or fusion devices can often be traumatic. If insufficient stabilization or incorrect anatomical alignment occurs, then revision surgery or on-going pain may be experienced by the patient.

There is a need for minimally invasive fracture fixation and spine fusion devices that can provide adequate stability through the use of screws and barbs, while maintaining a natural anatomical alignment during the healing process. If bone growth material is used, then the implant should limit the migration of this material from the fracture or fusion site.

Intramedullary nail devices using temperature effect to insert and fix a device in a bone are disclosed in U.S. Patent Application Publication No. 2010/0241120 to Bledsoe and U.S. Pat. No. 7,695,471 to Cheung et al. The Bledsoe device allows coolant to pass through the implant and into the body via the fracture, which can potentially flush away osteoblast. Osteoblast is believed to promote or accelerate the healing process and by flushing it away there may be a detrimental impact to the healing process. Cheung et al includes bone fixation without using other fastening elements but does not provide a method for maintaining the device in a chilled martensitic phase during implantation.

Minimally invasive interbody spine fusion devices that are introduced in a relatively straight configuration and form a curved configuration within the disc space have been disclosed. One generalized patent to limit the movement of flowable material introduced into or between tissue layers of the human spine U.S. patent application Ser. No. 07/666,227 Benvenue Medical, Inc. (Inventor, Laurent Schaller) The Schaller device prevents or substantially limits the movement of flowable material into vertebral material. However this device does not define any means for mechanical fixation.

In U.S. Pat. No. 8,206,423 Siegal et al has devised a device that utilizes hinges to allow deflection of each segment relative to adjacent segment, the device has a physical geometry which has an elongated element in the fully flexed state and a predefined curved configuration. However, this device defines an external method for delivery of osteogenic material.

Other attempts such as U.S. Pat. No. 8,162,942 focus on fixation barbs and other partial solutions, but have limited applicability and still fail to provide a truly minimally invasive approach, due to the device requiring installation through the joint surface which can result in long term degeneration of the joint surface. All previous attempts have failed to provide a complete solution, but have instead addressed only minimally invasive fixation, anatomical alignment, or the containment of bone growth material, and not all three. Solutions have been long sought but prior developments have not taught or suggested any solutions, and thus, solutions to these problems have long eluded those skilled in the art.

SUMMARY OF THE INVENTION

The claimed invention is directed to systems and methods for fixating or fusing bones that have an original shape that can be configured to deform into shapes that have circumferential lengths that remain substantially unchanged, and when inserted into the body returns to an original shape that matches the anatomy. Among the many different possibilities contemplated, one embodiment includes an implant which contains barbs or screws to minimize the possible migration of the implant and to provide added structural rigidity during the bone healing process.

Another embodiment of the invention includes an interbody spinal fusion device generally used for degenerative disc issues and for fusing vertebra together comprising a tubular member made of shape memory material. In one example, the tubular member and projections can comprise super-elastic material such as nitinol having an austenite start (As) temperature of about 5° C. and an austenite finish (Af) temperature of about 30° C.

Another embodiment may also contain open features on the inner annular surface. These open features permit bone graft or other bone growth material to be delivered down the longitudinal axis of the tubular construction and introduced into the center region while constraining the bone growth material from flowing to undesirable areas.

Other embodiments of the invention provide benefits that include the ability to match anatomical angles and curvatures.

An alternate embodiment can be comprised of a tubular implant made of a shape memory material that when chilled is maintained in a flexible state for insertion into a desired location within the body and when warmed to approximately body temperature has a rigid state, which allows the implant to provide adequate fixation.

The present invention further includes objects, features, aspects, and advantages in addition to or in place of those mentioned above. These objects, features, aspects, and advantages of the present invention will become more apparent from the following detailed description of preferred embodiments of the invention, along with the accompanying drawings.

BRIEF DESCRIPTION OF THE DRAWINGS

The invention is illustrated in the figures of the accompanying drawings which are meant to be exemplary and not limiting, in which like reference numerals are intended to refer to like components, and in which:

FIG. 25 is a flow chart of a method of use of the implant system for a fracture fixation embodiment of the present invention.

DETAILED DESCRIPTION OF THE INVENTION

Figure 1:
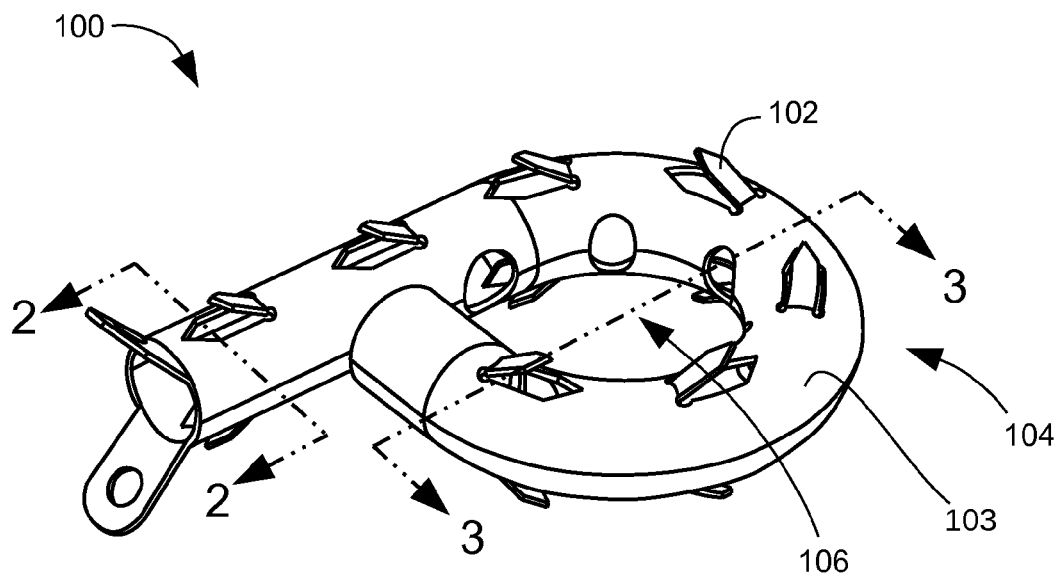
FIG. 1 is an isometric view of an implant system in a first embodiment of the present invention and in an original shape.

In the following description of the preferred embodiments, reference is made to the accompanying drawings that form a part hereof, and in which are shown by way of illustration, preferred embodiments in which the invention may be practiced. It is to be understood that other embodiments may be utilized and structural changes may be made without departing from the scope of the present invention.

The following preferred embodiments disclose an implant system implemented within various (elements used) for clarity and descriptive convenience. The implant system is described in sufficient detail to enable those skilled in the art to make and use the invention and provide numerous specific details to give a thorough understanding of the invention; however, it will be apparent that the invention may be practiced without these specific details.

In order to avoid obscuring the present invention, some well-known system configurations are not disclosed in detail. Likewise, the drawings showing embodiments of the system are semi-diagrammatic and not to scale and, particularly, some of the dimensions are for the clarity of presentation and are shown greatly exaggerated in the drawing FIGs. Generally, the invention can be operated in any orientation.

As used herein, the term "superior" is defined as above. The term "inferior" is defined as below. The term "nitinol" is defined as a shape memory and super-elastic metal. The term "austenitic" is defined as the rigid phase for nitinol. The term "martensitic" is defined as the soft or malleable phase for nitinol. The term "osteogenic" is defined as bone tissue formation. The term "lordosis" is defined as the inward curvature of a portion of the lumbar and cervical vertebral column.

The invention generally involves bone fixation or spinal fusion apparatuses that use super-elasticity or pseudo-elasticity and/or shape memory effect for bone fracture fixation or spinal fusion. A shape memory material such as a nickel titanium alloy material or nitinol can be used to provide these properties.

According to one embodiment of the invention, a nitinol implant system 1700 is treated thermally and mechanically such that it has one predetermined memory set shape. The implant system can be provided with one-way shape memory such that it can undergo deformation at a relatively cool temperature and then recover its preset memory shape upon heating above its austenite finish transformation temperature without requiring external mechanical forces. In a second embodiment, the implant system can be provided with two-way shape memory where the device has a shape that is reversible upon return of the temperature.

In a third embodiment, the implant system 400/2000 may rely on the materials super-elastic properties. For embodiments incorporating the use of super-elastic properties, the implant system is deformed and constrained in the deformed shape using a rigid mandrel. The rigid mandrel may be comprised of a rod or tube. The preferred embodiment would be comprised with the rigid mandrel tube being sized to fit within the inner diameter of the implant system. The inner diameter of the rigid mandrel tube being sized to fit over a guide wire.

According to one embodiment of the invention, the implant system 1700 can have a memory shape to which it returns when, for example, its temperature is increased to about an average body temperature after having been cooled below its austenite start temperature. The implant system for example, can be designed so that when cooled below about 5° C. it is in its martensitic state and when warmed above about 30° C. it returns to its austenitic state and preset memory set shape without requiring external mechanical forces. When cooled to its martensitic state, it is readily malleable and flexible, for introduction into the body. After the device is in its desired position, it is no longer cooled so that it can warm to the patient's body temperature (e.g., above 30° C.) where the device returns to its austenitic state and its memory set shape. It is more rigid in the austenitic state and provides stable support.

The implant system 1800 can be, for example, an intramedullary fixation device. It can be sized and configured to treat various fractured bones. For example, it can be sized and configured to treat a fractured humerus, radius, ulna, tibial, femeral or clavicle bone. In one embodiment, it is introduced through a bony projection of the bone. For example, in the case of the humerus bone, it can be bent to accommodate a curved bore made through the epicondyle or greater tuberocity, and then advanced into the intramedullay canal. Among the many advantages of this approach is that it reduces surgical trauma as compared to introducing the device at the end of the treated bone, potentially compromising the joint surface. Typically, the implant system would have a memory set configuration that aligns with the medullary canal. For the femeral and tibial bones, the memory set shape is relatively straight while for other bones like the clavicle it may have a curve that aligns with the anatomical shape of the medullary canal.

Figure 4:
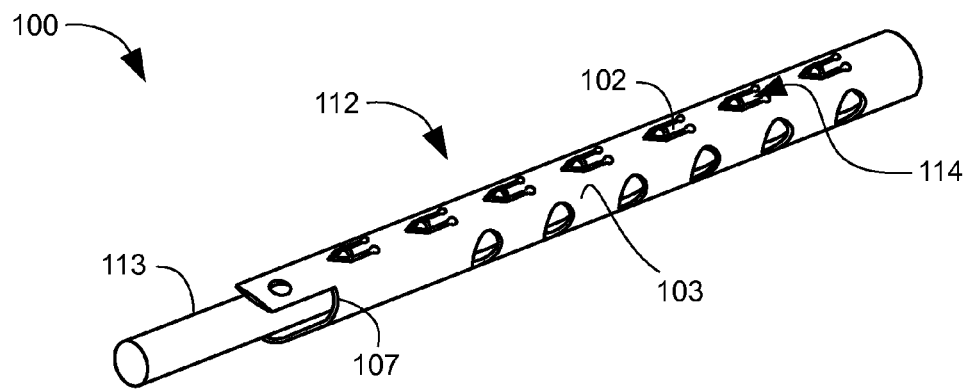
FIG. 4 is an isometric view of the implant system of FIG. 1 in a deformed shape.

The implant system 100 can be deformed into a deformed shape 112 of FIG. 4 having a circumferential length 107 of FIG. 4. The circumferential length 107 of the deformed shape 112 should be substantially similar to the circumferential length 108 of FIG. 2 of the original shape 104 of FIG. 1. For the purposes of this application a substantially similar circumferential length is defined as a circumferential length between the deformed shape 112 and original shape 104 of no more than a factor of 1.5.

The circumferential length 107 of the deformed shape 112 and the circumferential length 108 of the original shape 104 can vary for example when the implant system 104 is loaded onto a mandrel 113 of FIG. 4. The mandrel 113 can cause the implant system 104 to deform and slightly increase the circumferential length 107 of the deformed shape 112; however, it should be noted that the increase in the circumferential length 107 of the deformed shape 112 by the mandrel 113 is not substantially different but is substantially similar to the circumferential length 108 of the original shape 104.

The implant may be manufactured from a porous shape memory material. The benefit of the porous material is that it permits osteo-integration. Other means of achieving osteo integration by coating the implant with hydroxyapatite-(HA) or other bio-compatible coatings that promote osteo integration is also contemplated.

Referring now to FIG. 1, therein is shown an isometric view of an implant system 100 in a first embodiment of the present invention and in an original shape 104. In this embodiment, the implant has barbs 102 that extend radially outward from a main body 103 of the implant system 100. The main body 103 of the implant systems 100 for spine fusion will typically take on a general "p" shape configuration when in the original shape 104. The center 106 of the "p" configuration can act as a receptacle for bone graft or other osteogenic material. This receptacle region provides the benefit of containing or limiting the migration of the osteogenic material.

Figure 2:
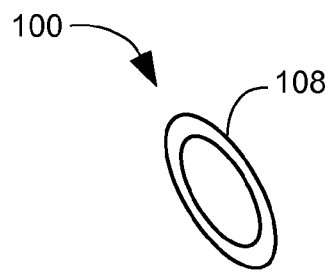
FIG. 2 is a cross-sectional view of the implant system of FIG. 1 along the line 2-2.

Referring now to FIG. 2, therein is shown a cross-sectional view of the implant system 100 of FIG. 1 along the line 2-2. This cross-section shows how the original shape 104 of FIG. 1 of the implant system 100 has been set such that it forms an ellipse 108 with the major axis in the horizontal plane and the minor axis in the vertical plane.

Figure 3:
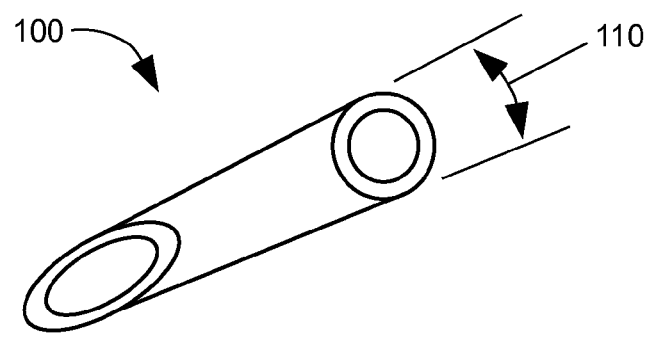
FIG. 3 is a cross-sectional view of the implant system of FIG. 1 along the line 3-3.

Referring now to FIG. 3, therein is shown a cross-sectional view of the implant system 100 of FIG. 1 along the line 3-3. This cross-section demonstrates how the implant system's 100 original shape 104 of FIG. 1 can be formed to have a lateral angle 110 similar to the anatomical angle of the disc between two adjacent vertebrae. By having the original shape 104 of the implant system 100 that mimics the disc anatomical angle it provides the benefit of being able to adjust the spine angle for people who are affected by lordosis.

Referring now to FIG. 4, therein is shown an isometric view of the implant system 100 of FIG. 1 in a deformed shape 112. Relying on the super-elastic properties of the material, the main body 103 of the implant system 100 can be deformed, the deformed shape 112 can include a relatively straight shape. Belts 114 can be used to constrain the barbs 102 in the deformed shape 112, which includes a retracted state which aids in the delivery of the implant system 100 into the body.

Figure 5:
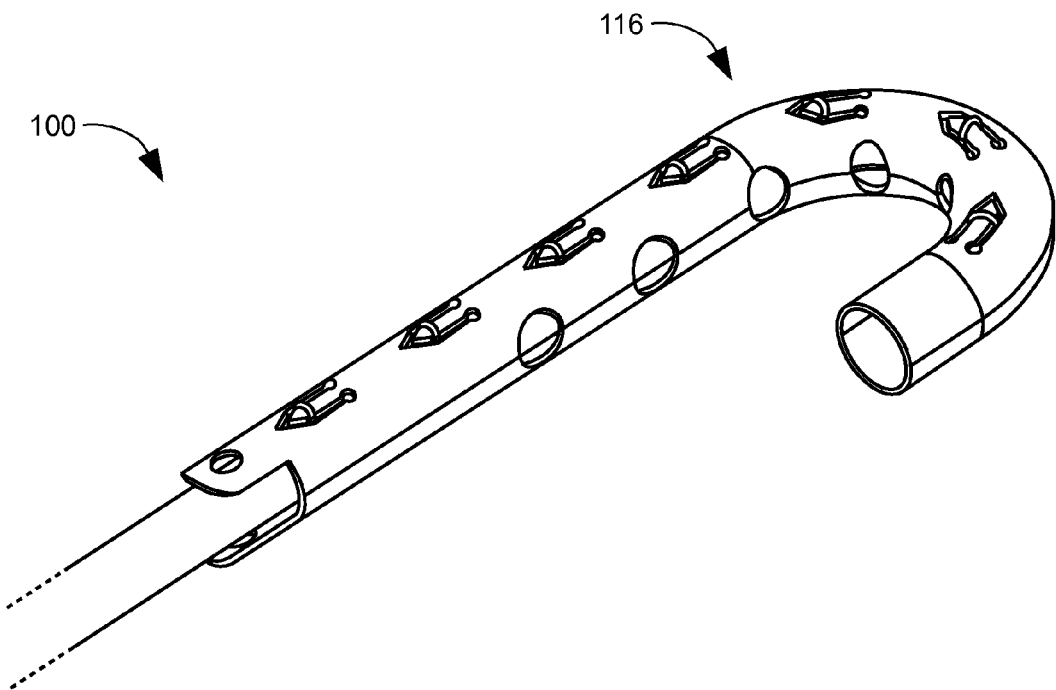
FIG. 5 is an isometric view of the implant system of FIG. 1 during a loading step of use.

Referring now to FIG. 5, therein is shown an isometric view of the implant system 100 of FIG. 1 during a loading step of use. As the implant is off-loaded from the mandrel 113, the implant system 100 begins to return to its original shape 104 without requiring external mechanical forces and is shown in a partially deformed shape 116.

Figure 6:
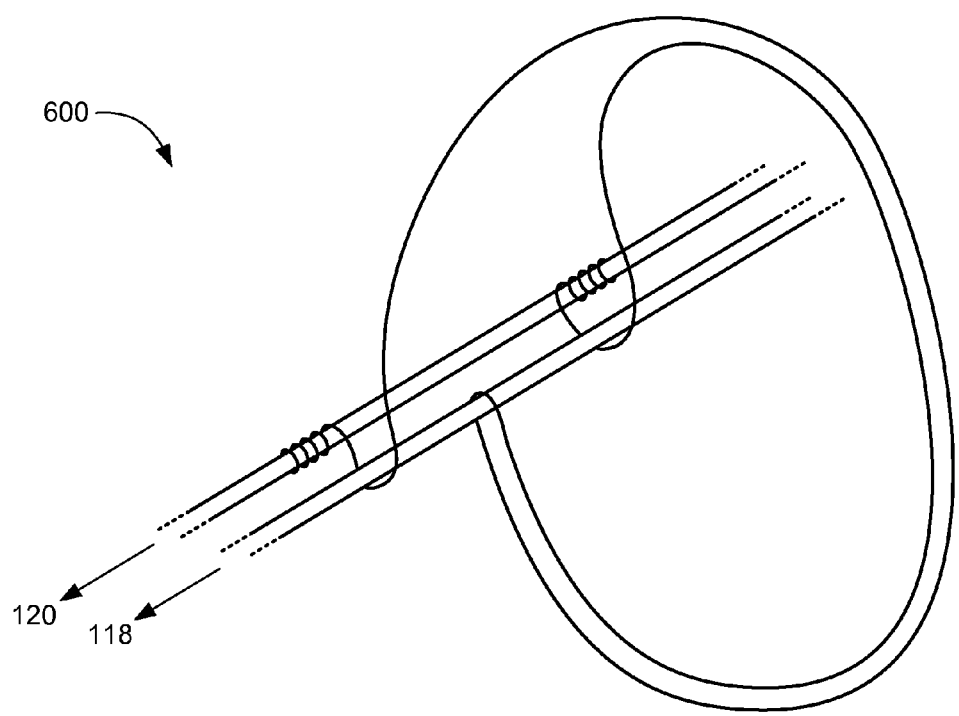
FIG. 6 is a schematic view of a retention belt for use with an embodiment of the present invention.

Referring now to FIG. 6, therein is shown a schematic view of a retention belt system 600 for use with an embodiment of the present invention. The belt system 600 of this design may be used to constrain the barbs 102 of FIG. 1 in the deformed shape 112 when the barbs 102 are retracted. Upon withdrawing a release wire 118, the belt system 600 is released permitting the barbs 102 to extend radially outward in their original shape 104 without requiring external mechanical forces. After the belts have been released and the barbs have extended radially outward, the belt system 600 may be removed from the implant system by withdrawing the belt cable 120.

Figure 7:
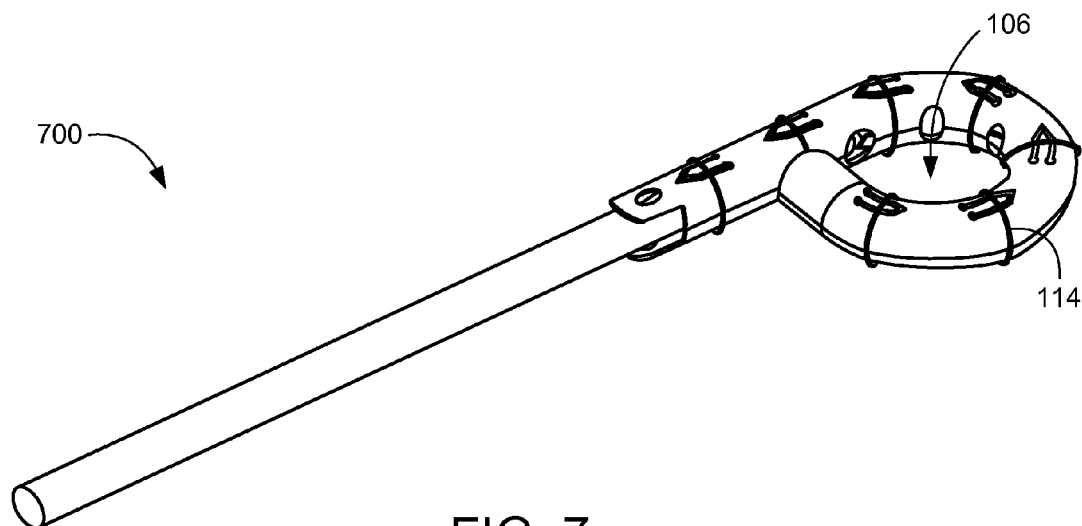
FIG. 7 is an isometric view of an implant system in a second embodiment of the present invention and in a partially deformed shape.

Referring now to FIG. 7, therein is shown an isometric view of an implant system 700 in a second embodiment of the present invention and in the partially deformed shape 116. In this FIG. the belts 114 are shown in an alternate configuration that is on the outside of the implant system 700 rather than within the lumen of the implant system 100 of FIG. 1. The implant system 700 has been partially deployed to the point where the receptacle 106 for osteogenic material has been formed.

Figure 8:
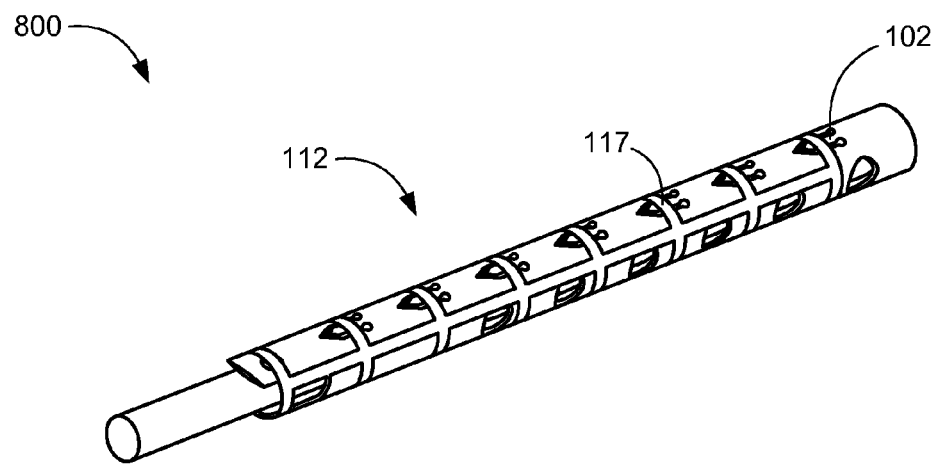
FIG. 8 is an isometric view of an implant system in a third embodiment of the present invention and in a deformed shape.

Referring now to FIG. 8, therein is shown an isometric view of an implant system 800 in a third embodiment of the present invention and in the deformed shape 112. In this embodiment, the belts 114 of FIG. 1 used for retaining the barbs 102 have been replaced by a banded sleeve 117. The banded sleeve 117 can be positioned with bands over the barbs 102 to constrain them in the deformed shape 112 and being retracted for ease of insertion into the desired location.

Figure 9:
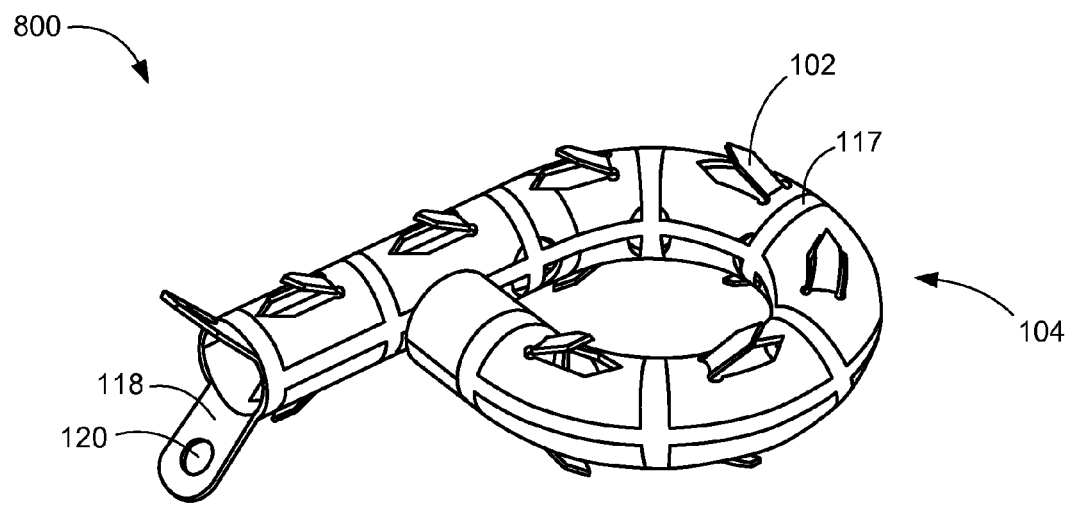
FIG. 9 is an isometric view of an implant system of FIG. 8 in an original shape.

Referring now to FIG. 9, therein is shown an isometric view of an implant system 800 of FIG. 8 in an original shape 104. This FIG. illustrates the banded sleeve 117 in an alternate position with the bands of the banded sleeve 117 positioned off the barbs 102. With the bands not constraining the barbs 102, the barbs 102 are free to expand radially to their original shape 104, thus providing fixation of the implant system 800. Additionally, tabs 118 with holes 120 that are sized to accept bone screws may return to their original shape 104.

Figure 10:
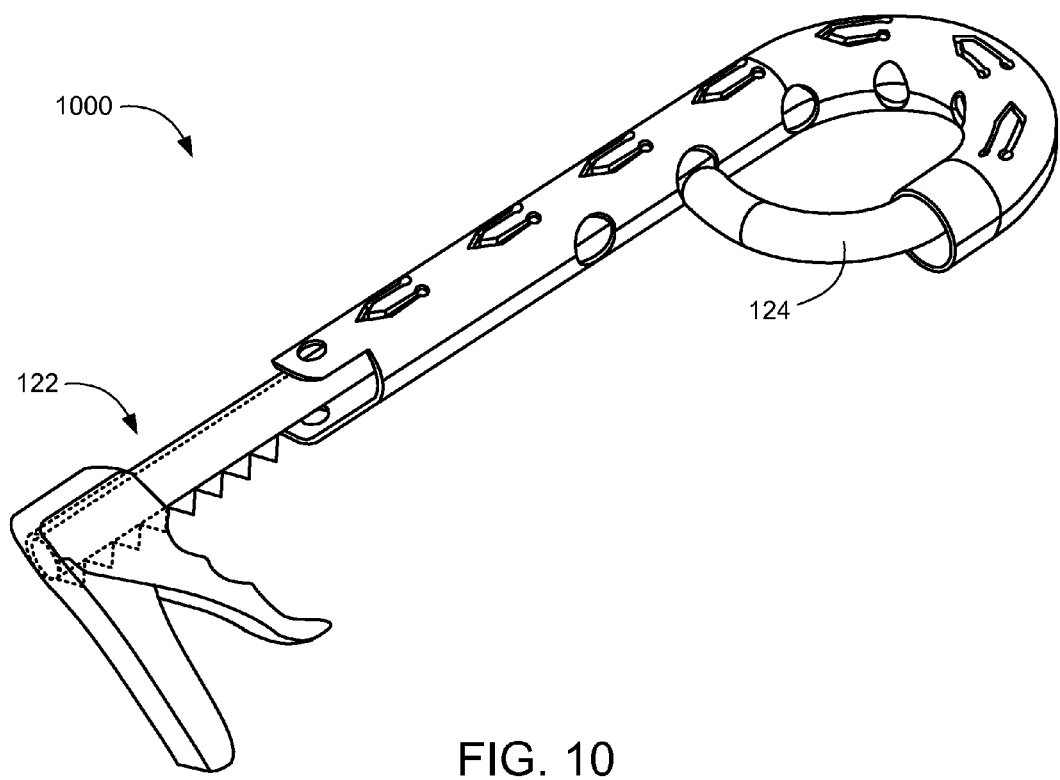
FIG. 10 is an isometric view of the implant system in a fourth embodiment of the present invention during a loading step of use.

Referring now to FIG. 10, therein is shown an isometric view of the implant system 1000 in a fourth embodiment of the present invention during a loading step of use. This FIG. demonstrates the use of a ratcheting mechanism 122 that can be used to off-load the implant system 1000 from a mandrel 124. As with other embodiments, including implant systems 700 and 800, the ratcheting mechanism 122 may be incorporated. An alternate off-loading mechanism may include a linear screw which is not shown.

FIG. 10 also illustrates the use of the mandrel 124 such as a guide wire mandrel that can provide directional guidance of the implant system 1000 assuming the implant system 1000 has been chilled and is in malleable martensitic state. The chilling method is further illustrated in FIG. 17.

Figure 11:
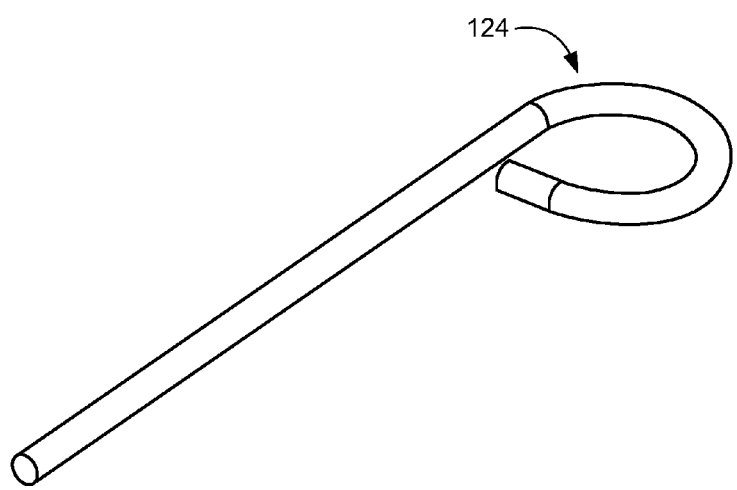
FIG. 11 is an isometric view of a guide-wire for use with an embodiment of the present invention.

Referring now to FIG. 11, therein is shown an isometric view of the mandrel 124 for use with an embodiment of the present invention. This mandrel 124 may be made of nitinol or other shape memory material. To maintain rigidity of the mandrel 124 the autenetic finish (Af) temperature of this component should be maintained below the temperature of the chilling fluid. Adjustments to the Af temperature can be achieved and is known to those skilled in the art.

Figure 12:
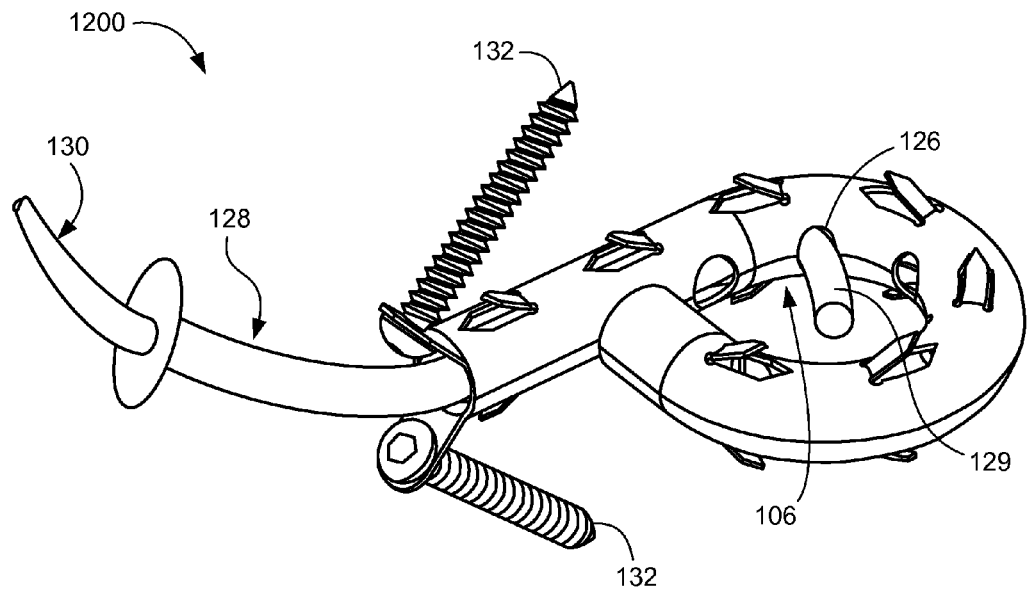
FIG. 12 is an isometric view of an implant system in a fifth embodiment of the present invention and in an original shape during an osteogenic material injection step of use.

Referring now to FIG. 12, therein is shown an isometric view of an implant system 1200 in a fifth embodiment of the present invention and in the original shape 104 during an osteogenic material injection step of use. This FIG illustrates one possible method of injecting osteogenic material into the center 106 or receptacle region. By using a flexible syringe 128. The end of the flexible syringe 129 can be sent through a port 126 that has been designed into the implant system 1200. Assuming the barrel of the flexible syringe 129 has been filled with osteogenic material, it can be injected into the receptacle region or the center 106 using the plunger 130. Additionally, bone screws 132 can be installed through the tabs 118 and into the superior and inferior vertebrae. The benefit of the flexible syringe 129 is that it permits directing the osteogenic material to desired locations. The addition of bone screws 132 can prove beneficial for providing increased rigidity and fixation.

Figure 13:
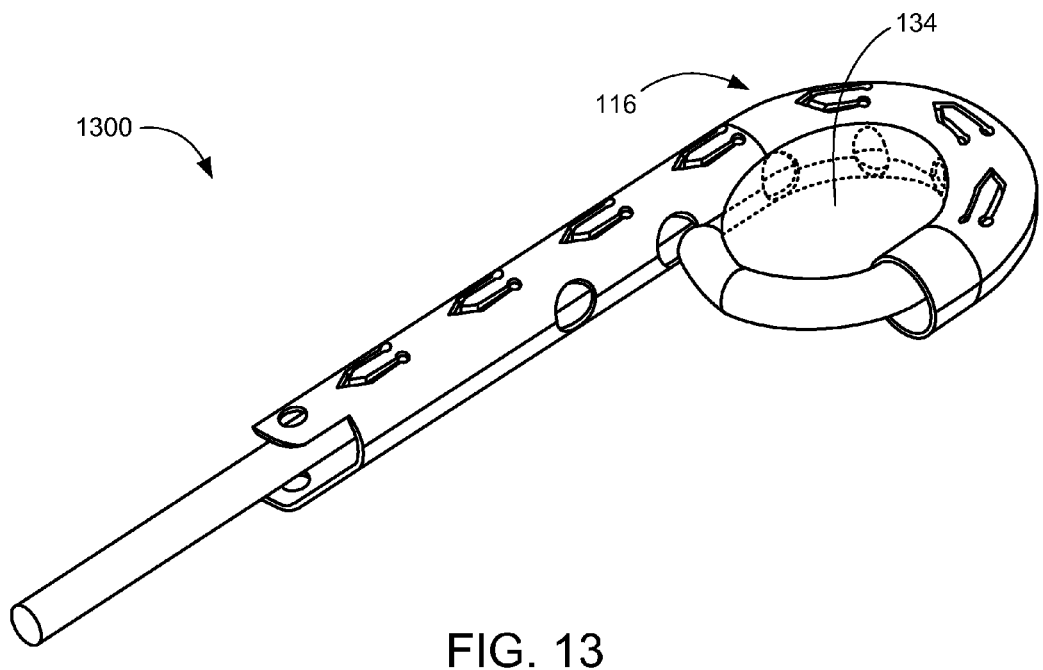
FIG. 13 is an isometric view of an implant system in a sixth embodiment of the present invention and in a partially deformed shape during an insertion step of use.

Referring now to FIG. 13, therein is shown an isometric view of an implant system 1300 in a sixth embodiment of the present invention and in the partially deformed shape 116 during an insertion step of use. This FIG illustrates the approach where the osteogenic material 134 has been placed prior to the introduction of the implant system 1300. The implant system 1300 can then wrap around the osteogenic material thus minimizing any migration of the said material.

Figure 14:
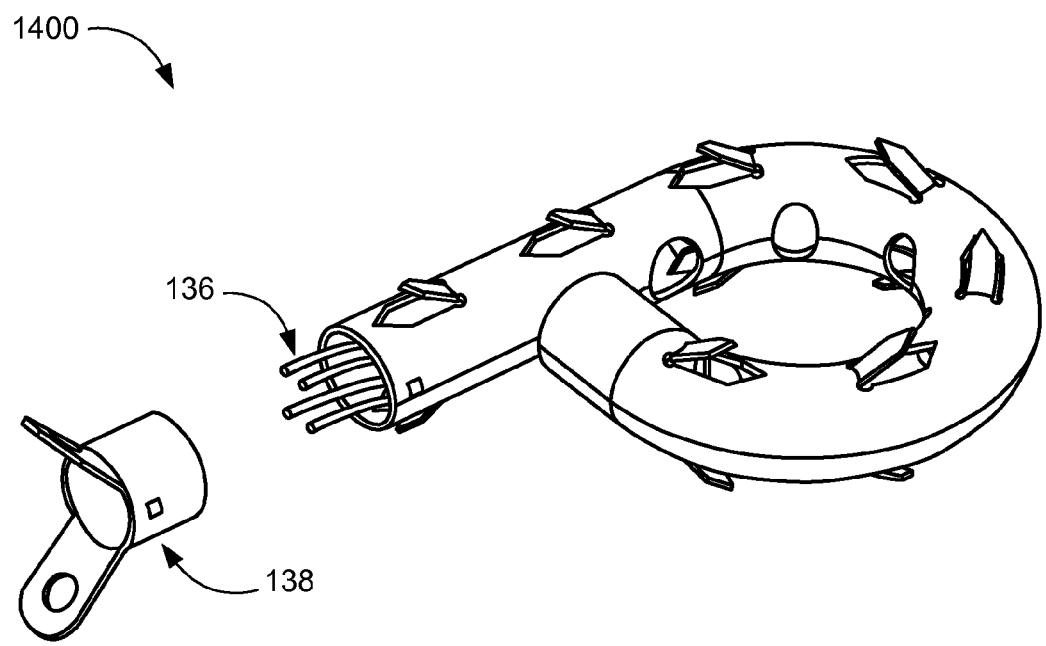
FIG. 14 is an isometric view of an implant system in a seventh embodiment of the present invention and in an original shape.

Referring now to FIG. 14, therein is shown an isometric view of an implant system 1400 in a seventh embodiment of the present invention and in the original shape 104. This FIG. illustrates how wires 136 or other semi-rigid material can be placed within the center lumen of the implant system 1400 to provide the added benefit of minimizing any compression of the implant when bending or compressive loads are applied. Alternatives to the wires 136 that can provide compressive rigidity to the implant system 1400 include rods or bone cement PMMA (polymethyl methacrylate). A cap 138 may be installed onto the end of the implant system 1400 to minimize the migration of any rigid filler material and to act as a fixation element for the bone screws 132 of FIG. 12 that may be placed into the superior and inferior vertebrae.

Figure 15:
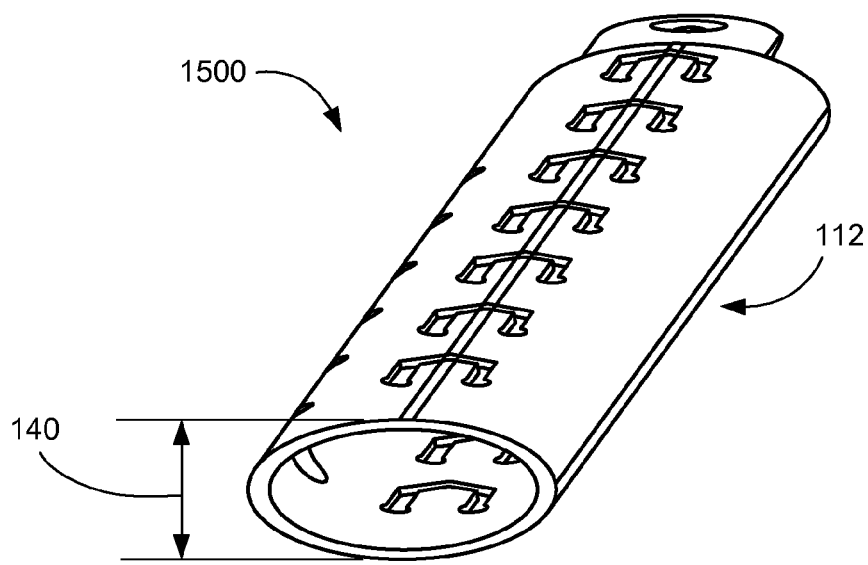
FIG. 15 is an isometric view of an implant system in an eighth embodiment of the present invention and in a deformed shape.

Referring now to FIG. 15, therein is shown an isometric view of an implant system 1500 in an eighth embodiment of the present invention and in the deformed shape 112. This FIG. illustrates how an implant system 1500 may be deformed in the vertical plane 140 to reduce the profile of the implant system 1500 such that it may be introduced into areas with minimal vertical accessibility.

Figure 16:
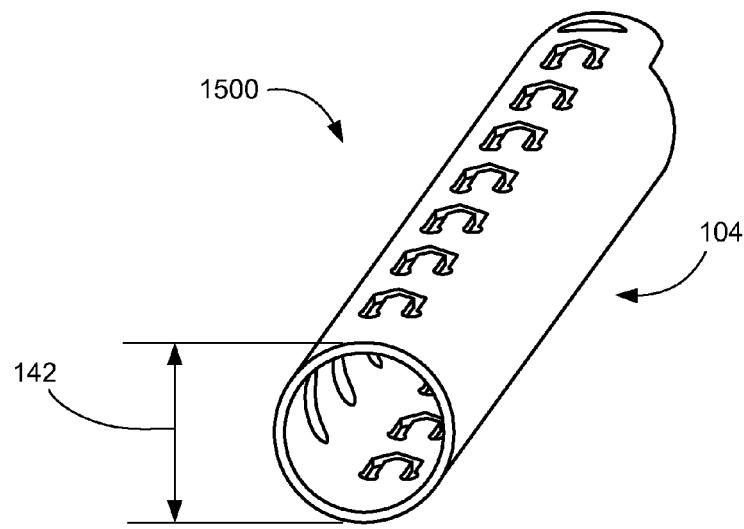
FIG. 16 is an isometric view of the implant system of FIG. 15 in an original shape.

Referring now to FIG. 16, therein is shown an isometric view of the implant system 1500 of FIG. 15 in the original shape 104. This FIG. illustrates the implant systems' 1500 return to its original profile 142 without requiring external mechanical forces, where the height of the original profile 142 is greater than the height of a profile of the deformed shape 112 of FIG. 15 deformed in the vertical plane 140 of FIG. 15 and thus providing the benefit of distraction or separating force between adjacent vertebrae.

Figure 17:
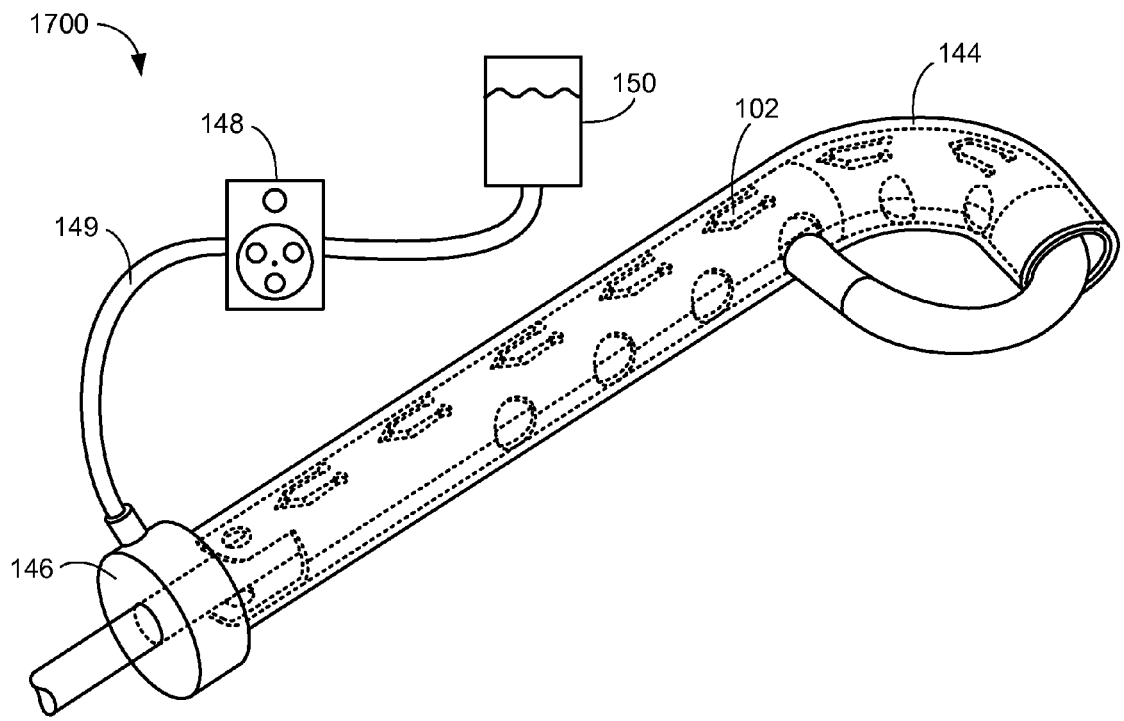
FIG. 17 is an isometric view of an implant system in a ninth embodiment of the present invention and in a partially deformed shape.

Referring now to FIG. 17, therein is shown an isometric view of an implant system 1700 in a ninth embodiment of the present invention and in the partially deformed shape 116. This FIG. illustrates the embodiment where a chilled fluid reservoir 150 can be circulated through the implant system 1700 to maintain the implant system 1700 in a flexible martensitic phase. Although one suitable fluid source (the fluid reservoir 150) and pump 148 for chilling the implant system 1700 is diagrammatically shown, it should be understood that other mechanisms for circulating fluid through the implant system can be used. Thus, the fluid reservoir 150 can be a bag (e.g., I.V. like bag) of chilled sterile saline that is placed in an ice bath. Once the saline is sufficiently cool, a standard I.V. plastic tube 149 would be used to connect it to flush port 146. The pump 148 can be a peristaltic pump located outside the fluid reservoir 150 and once turned on it would create a suction pulling chilled fluid from the fluid reservoir 150 typically a sterile bag of saline, through the pump and out to the implant system 1700. The pump 148 would be clamped onto the plastic tube 149 and when turned on, fluid would be transferred from the bag or the fluid reservoir 150, through the plastic tube 149 and into the implant system 1700.

A sheath 144 with the attached flush port 146 constrains the chilled fluid around the implant system 1700. The sheath 144 also acts in a beneficial function as a constraint to maintain the barbs 102 in a retracted state. In this manner, a cooling fluid can be circulated in the implant system 1700 during insertion so that the implant system 1700 remains flexible throughout the insertion process and the barbs 102 do not prematurely move to their memory shape configuration (the original shape 104 of FIG. 1) and anchor the implant system 1700 before it is in position. The sheath 144 also provides a smooth surface for insertion and can be readily withdrawn after the implant system 1700 is in the desired position.

Once the implant system 1700 has been properly positioned, the pump 148 may be turned off and the sheath 144 removed, thus permitting the implant system 1700 to warm to body temperature (approximately 37° C.). The implant system's austenitic finish temperature Af should be processed so that it remains below body temperature and thus the implant becomes structurally rigid.

Figure 18:
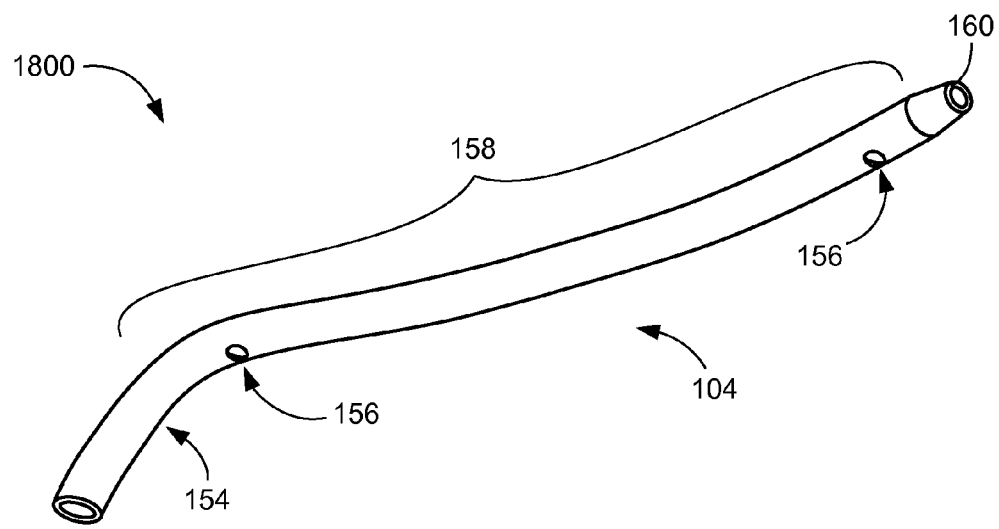
FIG. 18 is an isometric view of an implant system in a tenth embodiment of the present invention and in an original shape.

Referring now to FIG. 18, therein is shown an isometric view of an implant system 1800 in a tenth embodiment of the present invention and in the original shape 104. This FIG. illustrates one preferred embodiment for a fracture fixation device. The implant system 1800 may have a curved end 154 which allows access to the medullary canal for certain long bones without disturbing a joint surface. However, the curved end 154 is not provided on all designs. According to another embodiment, the bone fixation device can have a straight shape without the curved end 154 when being used in an ulna bone. In a further embodiment, the bone fixation device can have an S-shape without the curved end 154 when being used in a clavicle. Transverse holes 156 may be designed into the implant system 1800 for the placement of bone screws.

The implant system 1800 may also be designed to have a radius of curvature 158 that mimics the anatomy of the fractured bone. Since many bones within the body have one or more curvatures, in one or more planes, the benefit of this embodiment is that the implant system 1800 may be inserted into the bone without distorting or applying undue stress to the bone.

In addition, the implant system 1800 is made from a tubular construct; it may be used in conjunction with a guide wire. A conical tip 160 may be designed into the implant system 1800 to act as an aid for inserting the implant into the medullary canal of the bone and across the fracture site.

Figure 19:
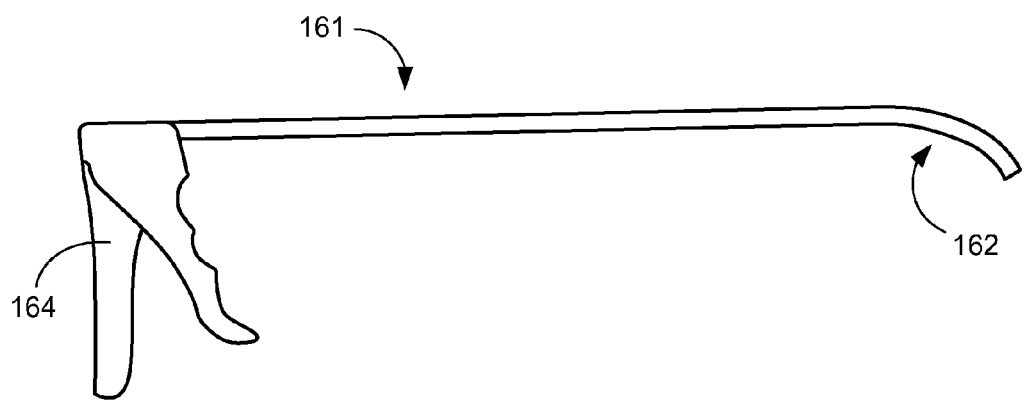
FIG. 19 is a side view of a mandrel for use with an embodiment of the present invention.

Referring now to FIG. 19, therein is shown a side view of a mandrel 161 for use with an embodiment of the present invention. The mandrel 161 is illustrated with a curved tip 162. The curved tip 162 allows for accessing the medullary canal of the bone via the side of the bone. The benefit of accessing the medullary canal from the side is that it eliminates the need to excise the joint surface which can increase the patient's risk of developing arthritis. The mandrel 161 may also contain a ratcheting handle 164 or other means, including a linear screw, to mechanically transfer the implant system 1800 from the mandrel 161 into the medullary canal.

Figure 20:
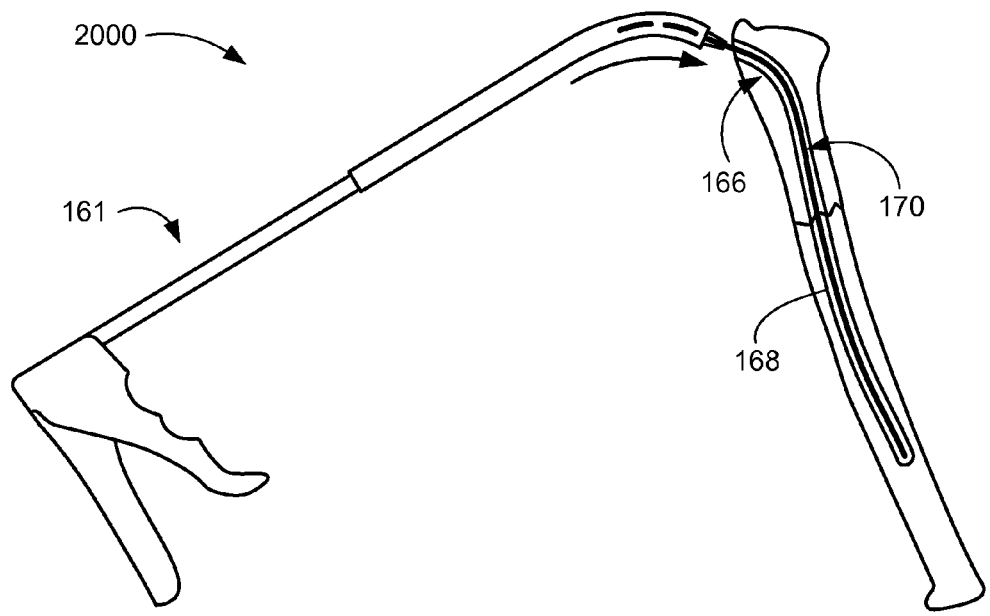
FIG. 20 is a side view of the implant system of FIG. 18 before an insertion step of use.

Referring now to FIG. 20, therein is shown a side view of the implant system 2000 of FIG. 18 before an insertion step of use. This FIG. illustrates the implant system 2000 that may be deformed and loaded onto a mandrel 161. A curved access hole 166 may be prepared within the fractured bone providing access to the medullary canal 168. A guide wire 170 may be inserted into the medullary canal 168 and the implant system 2000 and the mandrel 161 may be threaded over the guide wire 170.

Figure 21:
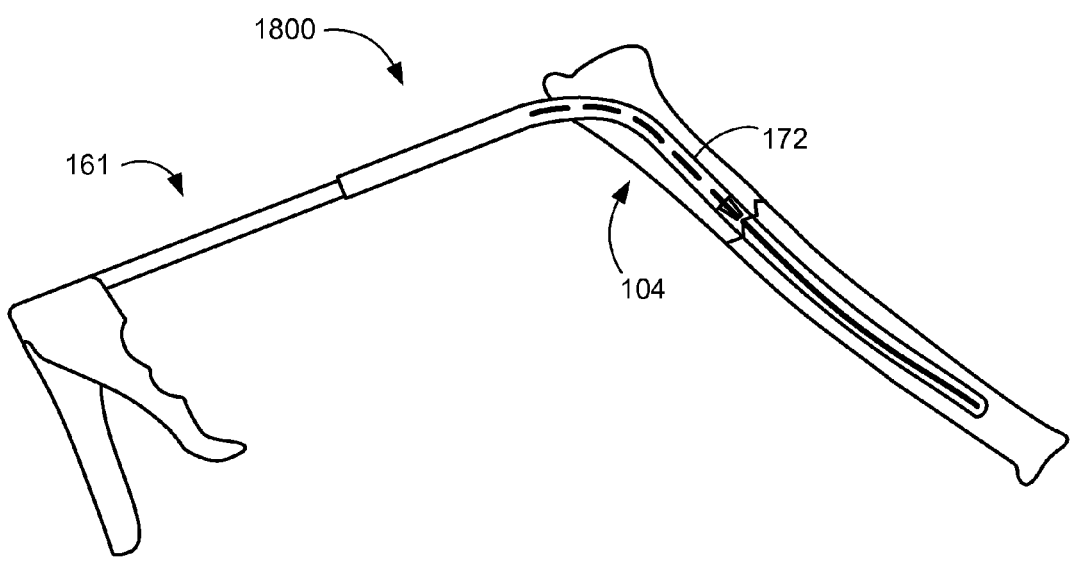
FIG. 21 is a side view of the implant system of FIG. 18 during an insertion step of use.

Referring now to FIG. 21, therein is shown a side view of the implant system 1800 of FIG. 18 during an insertion step of use. This FIG. illustrates how the implant system 1800 has been partially off-loaded from the mandrel 161. As the implant system 1800 is transitioned off the mandrel 161, the part 172 of the implant system 1800 that is not in contact with the mandrel 161 is shown returning to its original shape 104 without requiring external mechanical forces.

Figure 22:
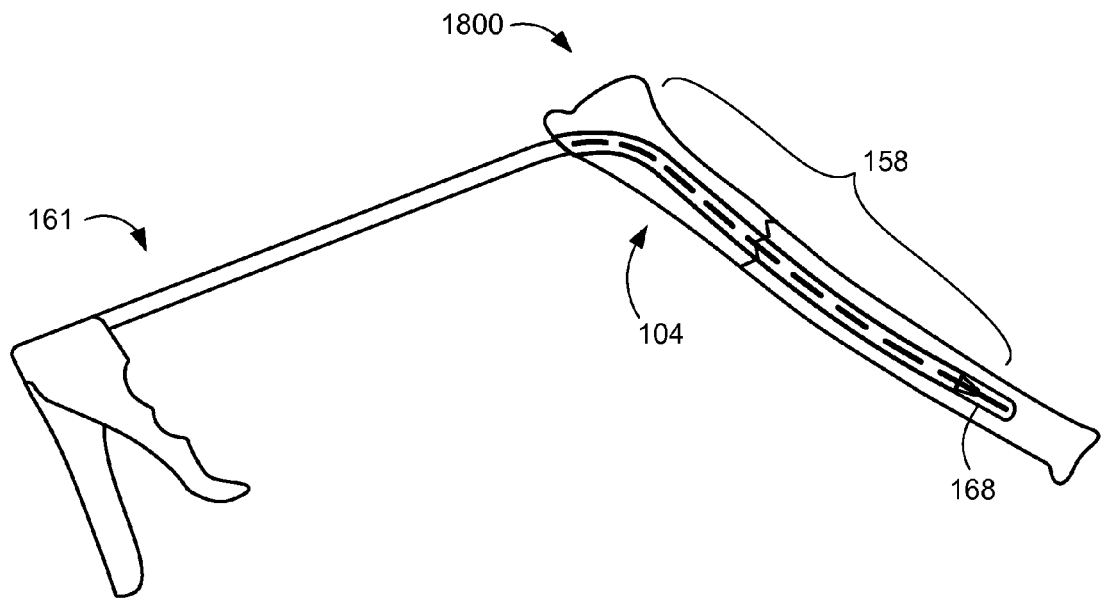
FIG. 22 is a side view of the implant system of FIG. 18 after an insertion step of use.

Referring now to FIG. 22, therein is shown a side view of the implant system 1800 of FIG. 18 after an insertion step of use. This FIG. illustrates how the implant system 1800 has been fully advanced into the medullary canal 168. The implant system 1800 has returned to its original shape 104 having the curvature 158 that matches the anatomical shape of the fractured bone. At this point the guide wire 170 of FIG. 21 and mandrel 161 may be removed.

Figure 23:
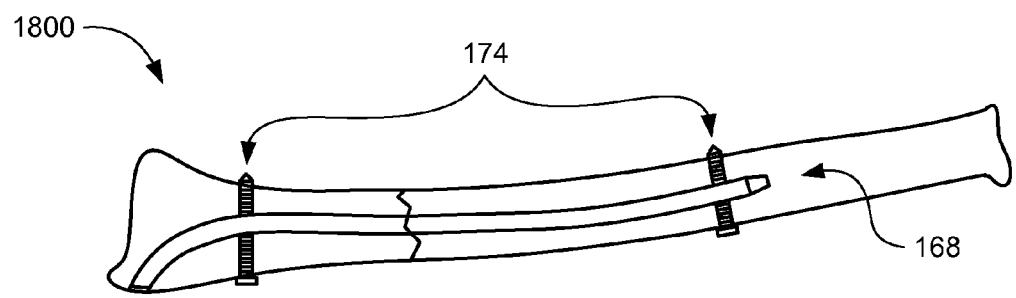
FIG. 23 is a side view of the implant system of FIG. 18 after an installation step of use.

Referring now to FIG. 23, therein is shown a side view of the implant system 1800 of FIG. 18 after the installation process. Illustrated in this FIG. is the use of transverse bone screws 174 that fixate the implant system 1800 within the medullary canal 168 and thus providing the benefit of creating a rigid scaffold during the bone healing process.

Figure 24:
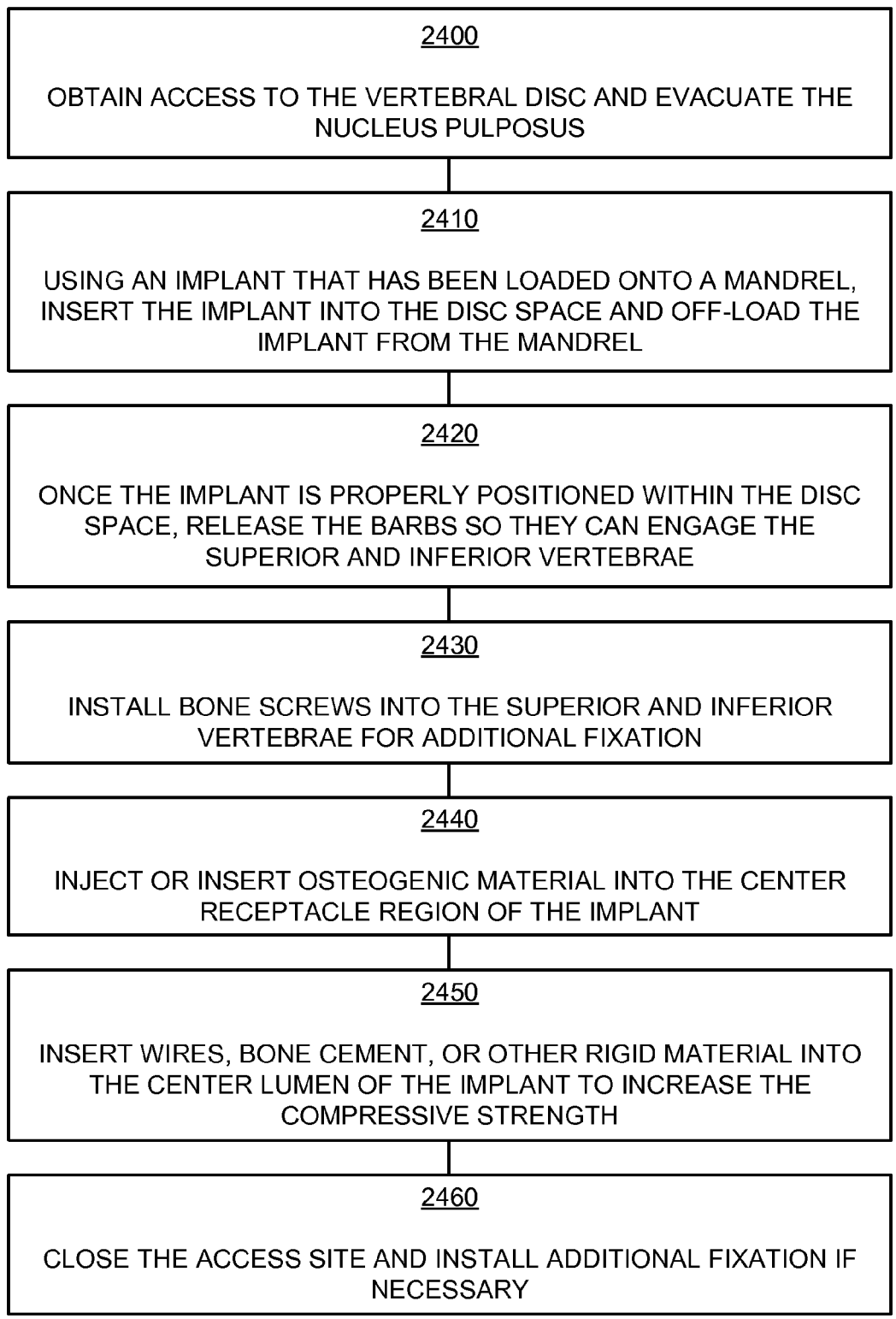
FIG. 24 is a flow chart of a method of use of the implant system for a spine fusion embodiment of the present invention.

Referring now to FIG. 24, therein is shown a flow chart of a method of use of the implant system for a spine fusion embodiment of the present invention. This flow chart is a descriptive explanation of the installation procedure for spine fusion. In the first step 2400, access is gained to the vertebral disc and the nucleus pulposus (center disc material) is evacuated to provide space for the implant. In the second step 2410, an implant that has been loaded onto a mandrel is inserted into the disc space and using either a ratchet, linear screw, or other mechanical means, the implant is off-loaded from the mandrel where the implant returns to its original configuration. In the third step 2420, barb constraints (belts/sleeves/or other mechanical means) are removed thus allowing the barbs to engage into the superior and inferior vertebrae. In the fourth step 2430, bones screws may be installed into the superior and inferior vertebrae providing additional fixation. In the fifth step 2440, osteogenic material including autograft, allograft, or bone morphogenic protein (BMP) can be injected or inserted into the center receptacle region of the implant. In the sixth step 2450, wires, a rod, bone cement, or other structurally rigid filler material is placed within the center lumen of the implant. This filler material increases the compressive strength of the implant when anatomical loads are applied. In the seventh step 2460, the access to the vertebral disc is closed and if deemed necessary, additional fixation such as pedicle screws with rods may be installed.

Referring now to FIG. 25, therein is shown a flow chart of a method of use of the implant system for a fracture fixation embodiment of the present invention. This flow chart is a descriptive explanation of the installation procedure for fracture fixation. In the first step 2500, access to the medullary canal via a boney protrusion is obtained. Most often this access is obtained by creating a curved access path using a cutting tool that has radius of curvature similar to the curved end 154 of the implant. In the second step 2510, a guide wire is inserted into the access hole and advanced across the fracture site. In the third step 2520, the medullary canal may be reamed to ensure the implant fits within the canal. In the fourth step 2530, the implant system is inserted at the access site and off-loaded from the rigid mandrel. In the fifth step 2540, the guide wire is removed and transverse bone screws may be installed to provide bone fixation. In the sixth step 2550, the access site is closed and a cast or other stabilization method is used during the healing process.

Thus, it has been discovered that the implant system of the present invention furnish important and heretofore unknown and unavailable solutions, capabilities, and functional aspects.

The resulting configurations are straightforward, cost-effective, uncomplicated, highly versatile, accurate, sensitive, and effective, and may be implemented by adapting known components for ready, efficient, and economical manufacturing, application, and utilization.

While the invention has been described in conjunction with a specific best mode, it is to be understood that many alternatives, modifications, and variations will be apparent to those skilled in the art in light of the preceding description.

Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. A method comprising:
   obtaining an implant system with a main body having an original shape;
   deforming the main body of the implant system into a deformed shape having a circumferential length substantially similar to a circumferential length of the original shape;
   chilling the implant system to set the implant system in the deformed shape;
   inserting the implant system into a body; and
   wherein obtaining the implant system includes obtaining the implant system configured to return to the original shape inside the body based on super-elastic properties of the implant system.

2. The method of claim 1, wherein, inserting the implant system includes inserting the implant system for fusing vertebrae or fixating a bone.

3. The method of claim 1, wherein, inserting the implant system includes inserting the implant system into the body utilizing a mandrel, a ratchet, a linear screw, or a combination thereof.

4. The method of claim 1, wherein, chilling the implant system includes chilling the implant system by providing a chilled solution through a sheath around the implant system.

5. The method of claim 1, wherein, obtaining the implant system includes obtaining the implant system having barbs configured to extend radially outward in the original shape.

6. The method of claim 5, wherein, deforming the implant system includes deforming the barbs on the implant system with a sleeve, a belt, a sheath, or a combination thereof.

7. The method of claim 1, further comprising, injecting osteogenic material into the body through the implant system.

8. The method of claim 7, wherein, injecting the osteogenic material includes injecting the osteogenic material with a plunger through ports in the implant system.

9. The method of claim 1, further comprising, filling the implant system with a bundle of wires, a rod, bone cement, or a combination thereof for preventing the implant system from collapsing.

10. The method of claim 1, further comprising, fixing the implant system to a bone with a screw.

11. An implant system comprising:
    a main body having an original shape;
    wherein the implant system configured to:
       deform the main body into a deformed shape having a circumferential length substantially similar to a circumferential length of the original shape,
       set in the deformed shape when chilled,
       insert into a body, and
       return to the original shape inside the body based on super-elastic properties of the implant system; and
    a sheath for chilling the implant system by providing a chilled solution through the sheath around the implant system.

12. The implant system of claim 11, wherein, the implant system is configured to fuse vertebrae or fixate a bone.

13. The implant system of claim 11, wherein, the implant system is configured to insert with a mandrel, a ratchet, a linear screw, or a combination thereof.

14. The implant system of claim 11, further comprising, barbs extending radially outward in the original shape.

15. The implant system of claim 14, further comprising, a sleeve, a belt, a sheath, or a combination thereof for deforming the barbs in the deformed position.

16. The implant system of claim 11, wherein, the implant system is configured to inject osteogenic material into the body through the implant system.

17. The implant system of claim 16, further comprising, a plunger for injecting the osteogenic material through ports in the implant system.

18. The implant system of claim 11, further comprising, a bundle of wires, a rod, bone cement or a combination thereof within the implant system for preventing the implant system from collapsing.

19. The implant system of claim 11, wherein, the implant system is configured to accept bone screws that provide fixation.

* * * * *